(12) United States Patent
Maack (10) Patent No.: US 9,648,711 B2
(45) Date of Patent: May 9, 2017

(54) X-RAY DETECTOR PIXEL LAYOUT (71) Applicant: KONINKLIJKE PHILIPS N.V., Eindhoven (NL)

(72) Inventor: Hanns-Ingo Maack, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 87 days.

(21) Appl. No.: 14/403,597

(22) PCT Filed: May 28, 2013

(86) PCT No.: PCT/IB2013/054399
§ 371 (c)(1),
(2) Date: Nov. 25, 2014

(87) PCT Pub. No.: WO2013/190408
PCT Pub. Date: Dec. 27, 2013

(65) Prior Publication Data
US 2015/0139392 A1    May 21, 2015

Related U.S. Application Data

(60) Provisional application No. 61/661,959, filed on Jun. 20, 2012.

(51) Int. Cl.
*H05G 1/08* (2006.01)
*G01T 1/29* (2006.01)
*A61B 6/00* (2006.01)

(52) U.S. Cl.
CPC ........... *H05G 1/085* (2013.01); *A61B 6/4233* (2013.01); *G01T 1/2928* (2013.01)

(58) Field of Classification Search
CPC .......... A61B 6/00; A61B 6/42; A61B 6/4208; A61B 6/4233; A61B 6/4258; G01N 23/08;
(Continued)

(56) References Cited

U.S. PATENT DOCUMENTS 5,847,684 A  12/1998  Strik
6,133,954 A  10/2000  Jie et al.
(Continued)

FOREIGN PATENT DOCUMENTS

| DE | 102005060518 A1 | 8/2006 |
| DE | 102010027791 A1 | 10/2011 |
| WO | 2004063803 A1 | 7/2004 |

*Primary Examiner* — Jurie Yun (57) ABSTRACT

An X-ray detector comprises an array of pixels, each comprising a sensitive area, a body structure, and an electric circuitry. The sensitive areas are attached to, and arranged on, the body structure. The electric circuitry controls and reads out the sensitive areas and connects the sensitive areas with a processing unit. The sensitive areas provide an electric signal representing X-rays hitting the pixel. All pixels are provided in a pixel layout with a pixel layout scheme where the sensitive area is a first part of the pixel's surface that is contributing to the pixel's signal and a second part of the pixel's surface is irrelevant to contributing to the pixel's signal. To facilitate avoiding visual artifacts, the sensitive areas in a pattern in which at least a part of the pixels having the same pixel layout scheme such that the pixel layout of adjacent pixels is arranged differently.

16 Claims, 8 Drawing Sheets (58) Field of Classification Search
CPC ...... G01N 23/083; G01T 1/2928; H05G 1/08; H05G 1/085; H01L 27/14676; H01L 27/14643; H01L 27/14609; H01L 27/1461; H01L 27/14603; H01L 27/14605; H01L 27/14607; H04N 5/335
USPC ............... 378/19, 98.8; 250/208.1, 370.09
See application file for complete search history.

(56) References Cited

U.S. PATENT DOCUMENTS

| | | |
|---|---|---|
| 6,246,042 B1 | 6/2001 | Szydlowski |
| 7,495,228 B1 | 2/2009 | Albagli et al. |
| 7,710,477 B2 * | 5/2010 | Nam ................ H01L 27/14603 257/292 |
| 2002/0014592 A1 | 2/2002 | Rutten et al. |
| 2010/0148037 A1 | 6/2010 | Bogaerts et al. |
| 2011/0080492 A1 | 4/2011 | Matsuda et al. |

* cited by examiner

X-RAY DETECTOR PIXEL LAYOUT

CROSS-REFERENCE TO PRIOR APPLICATIONS

This application is the U.S. National Phase application under 35 U.S.C. §371 of International Application Serial No. PCT/IB2013/054399, filed on May 28, 2013, which claims the benefit of U.S. Application Ser. No. 61/661,959, filed on Jun. 20, 2012. These applications are hereby incorporated by reference herein.

FIELD OF THE INVENTION

The present invention relates to pixel layout of a detector, and relates in particular to an X-ray detector, a medical X-ray imaging system and a method for X-ray imaging.

BACKGROUND OF THE INVENTION

In the use of X-ray detectors, for example in wireless portable detectors, it has been shown that fixed anti-scatter grids are can be visible in the images. For improved image quality, complex image filters are provided to mitigate the problem. However, it has been shown that these measurements are connected with additional effort in terms of time or equipment and are thus related reduced economic disadvantageous. WO 2004/063803 A1 describes a detector with an array of pixels arranged in rows and columns in form of a matrix, where access lines are provided that run in zigzag fashion along diagonally of the matrix.

SUMMARY OF THE INVENTION

Thus, there may be a need to provide a facilitated way of avoiding artifacts in images provided by X-ray detectors.

The object of the present invention is solved by the subject-matter of the independent claims, wherein further embodiments are incorporated in the dependent claims.

It should be noted that the following described aspects of the invention apply also for the X-ray detector, the medical X-ray imaging system and the method for X-ray imaging.

According to a first aspect of the present invention, an X-ray detector is provided comprising a pixel array with a plurality of pixels, each of which comprises a sensitive area. The X-ray detector further comprises a body structure and an electric circuitry. The sensitive areas are attached to the body structure. The electric circuitry is provided to control and read out the sensitive areas and to connect the sensitive areas with a processing unit. The sensitive areas are configured to provide an electric signal representing X-ray radiation hitting the pixel. All pixels are provided in a pixel layout with a pixel layout scheme, where the sensitive area is a first part of the pixel's surface that is contributing to the pixel's signal and a second part of the pixel's surface is irrelevant to contributing to the pixel's signal. The sensitive areas are arranged on the body structure in a pattern in which at least a part of the pixels having the same pixel layout scheme is provided such that the pixel layout of adjacent pixels is arranged differently.

The pixel itself may be provided with a square form, or with a rectangle form or other form, such as a honeycomb form. The term "form" relates to the respective surface area of the sensitive area of the pixel, i.e. the pixel comprised of the first part and the second part. The second parts of adjacent pixels are arranged at different locations.

According to an exemplary embodiment, at least a part of the pixels is arranged such that the pixel layout of adjacent pixels is i) mirrored, and/or ii) rotated, in relation to each other.

According to an exemplary embodiment, the pixels are provided in rows in a first direction and in columns in a second direction. A different arrangement of the layout is provided in the first and the second direction for the at least part of the pixels, for adjacent pixels.

According to an exemplary embodiment, the pixels are provided in honeycomb structure with three repetition directions. A different arrangement of the layout is provided in all three repetition directions for the at least part of the pixels.

According to a further exemplary embodiment, for all pixels, adjacent pixels are provided in a different arrangement of the pixel layout, but with the same pixel layout scheme.

For example, the term "different arrangement" relates to a different layout orientation, for adjacent pixels.

According to an exemplary embodiment, all pixels are arranged such that the pixel layout scheme of adjacent pixels is i) mirrored, and/or ii) rotated, in relation to each other.

According to a second aspect of the present invention, a medical X-ray imaging system is provided, comprising an X-ray source, an X-ray detector, and a processing unit. The X-ray detector is provided as an X-ray detector according to one of the above mentioned examples.

The sensitive area may be provided as a photodiode, for example for indirect conversion. According to a further example, in case of direct conversion, a detector with selenium, for example, may be provided, where the sensitive area is forming an electrode.

According to a third aspect of the present invention, a method for X-ray imaging is provided, comprising the following steps:

a) generating X-ray radiation by an X-ray source;
b) radiating an object of interest with at least a part of the generated X-ray radiation;
c) receiving X-ray radiation that was at least partly attenuated by the object; and
d) converting the received X-ray radiation into an electrical signal by an X-ray detector according to one of the above mentioned examples.

According to an aspect of the present invention, the specific shape, so-to-speak, of a photodiode, or other pixel, is not changed, but the pixel layout is mirrored or rotated, or both, such that the design rules of the photodiode design, for example, and the design of the read out transistor does not need to be modified. As a benefit, less sensitivity to gridline depiction due to improved shift in variance of the line spread function is achieved. Thus, remaining software effort to remove the gridlines with software procedures is facilitated. As a result, a better image quality is achievable. According to a further aspect, in particular in relation with wireless portable detectors, the signal of a long and narrow line on the detector will be less dependent on the precise location in respect to the photodiodes, or sensitive areas. As a result, the gridlines of a fixed anti-scatter grid will be less visible.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 1 shows an exemplary embodiment of an X-ray detector in a side view or cross section in FIG. 1A and in a top view in FIG. 1B;

FIG. 2 shows different examples for a pixel layout scheme in FIGS. 2A to 2E;

FIG. 3 shows X-ray detector in a top view in one exemplary embodiment in FIG. 3A and another exemplary embodiment in FIG. 3B;

DETAILED DESCRIPTION OF EMBODIMENTS

Figure 1A:
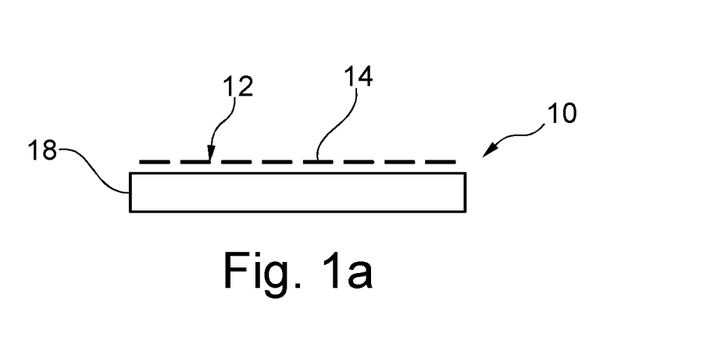
Figure 1B:
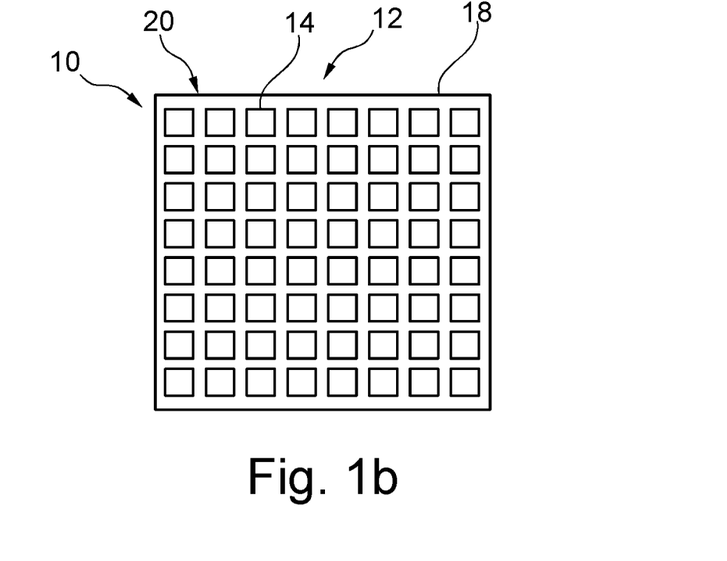

FIG. 1 shows an X-ray detector 10 in a cross section or side view in FIG. 1A and in a top view in FIG. 1B. A pixel array 12 with a plurality of pixels 14 is provided, each of which pixels 14 comprises a sensitive area 16 (see also FIGS. 2A to 2E and the respective below passages of the description). Further, a body structure 18 is provided, and an electric circuitry 20 (not further shown). The sensitive areas 16 are attached to the body structure 18. The electric circuitry is provided to control and read out the sensitive areas 16 and to connect the sensitive areas 16 with a processing unit (not further shown). The sensitive areas 16 are configured to provide an electric signal representing X-ray radiation hitting the pixel. All pixels are provided in a pixel layout with a pixel layout scheme 22, which is not further shown in FIGS. 1A and 1B, but which shall be described with reference to FIG. 2A.

The term "pixel layout scheme" refers to the sensitive areas 16 and the non-sensitive areas as a form of geometric figure. The term "pixel layout" refers to the way this geometric figure, or pixel layout scheme, is arranged for the respective pixel.

The sensitive area may be provided as a photodiode, in case of indirect conversion, or, in case of direct conversion, as a detector with selenium, an electrode, for example.

The layout scheme itself may be repeated for all pixels.

The term "arranged" relates to the orientation or positioning of the pixel layout scheme forming the pixel layout.

The electric circuitry may comprise read out transistors and the like.

Figure 2A:
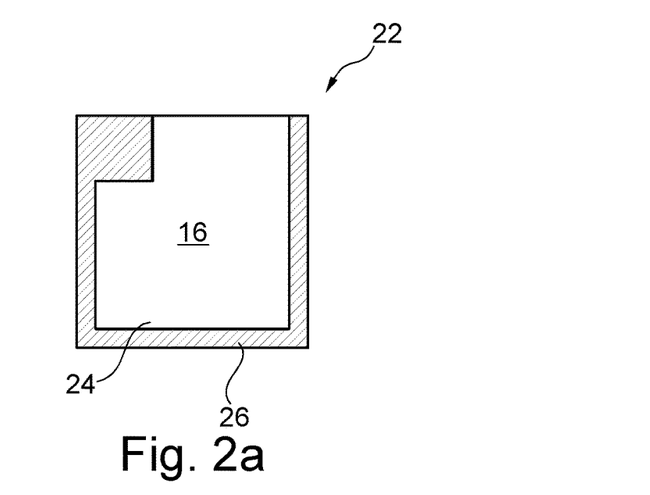

For example, as shown in FIG. 2A, the sensitive area 16 is a first part 24 of the pixel's surface that is contributing to the pixel's signal, and a second part 26 of the pixel's surface is irrelevant to contributing to the pixel's signal. The second part 26 is shown with a hashed pattern throughout FIGS. 2A, 2B, 2C, 2D, and 2E. The respective sensitive area 16, or first part 24, is left white.

FIG. 2 shows a square form of the pixel provided with portions of the second part 26 around three of the four edges.

Figure 2B:
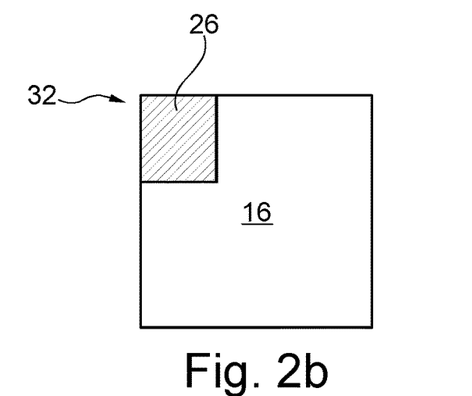
Figure 2C:
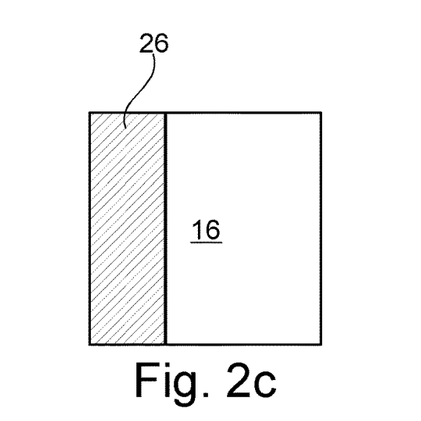

In FIG. 2B, the second part 26 is only provided in a corner. In FIG. 2C, the second part 26 is provided along one side.

Figure 2D:
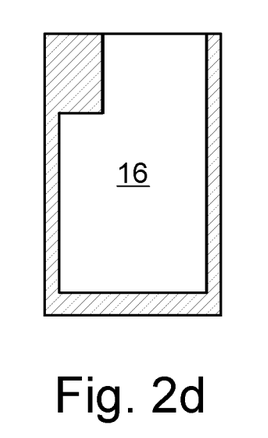

FIG. 2D shows a similar pixel layout with a pixel layout scheme 22 as FIG. 2A, but having the form of the pixel as a rectangle instead of a square.

Figure 2E:
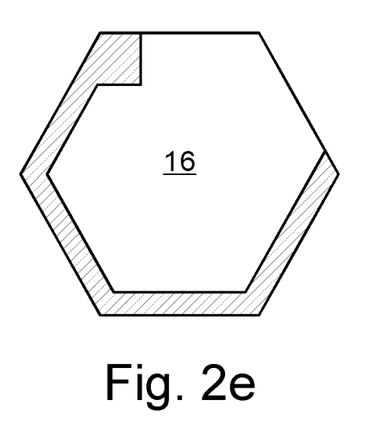

FIG. 2E shows a further example, in which the form of the respective singular pixel is shaped as a honeycomb with the second part 26 arranged along a portion of the surrounding layout.

As indicated above, the sensitive area 16 is also referred to as first part of a pixel. The sensitive area is also referred to as active area of the pixel.

The distance of the center point of two adjacent pixels is referred to as pixel pitch, which pixel pitch may be provided in a constant manner throughout the pixel array 12, or with a decreasing or increasing pixel pitch. For example, this can be equal in different directions, such as x- and y-direction. However, the pitch can also be different in different directions. The pitch may also be composed of different sub-pitches.

The pixel size is the size of the sensitive area. The sensitive area may be a rectangle with differing x- and y-sizes. The pixel's surface may be more complex, such as the sensitive area having a missing part in the corner of the rectangle (for example, see FIG. 2B).

According to a further example, the sensitive area, or active area may be L-shaped, as indicated in FIGS. 2A and 2D.

The sensitive area may be a photodiode, or an electrode in case of direct conversion, a detector with selenium, for example.

The layout scheme itself may be repeated for all pixels such that adjacent pixels, i.e. their pixel layouts, are differently arranged. The term "arranged" relates to the orientation or positioning of the pixel layout scheme.

The electric circuitry may comprise read out transistors and the like.

Figure 3A:
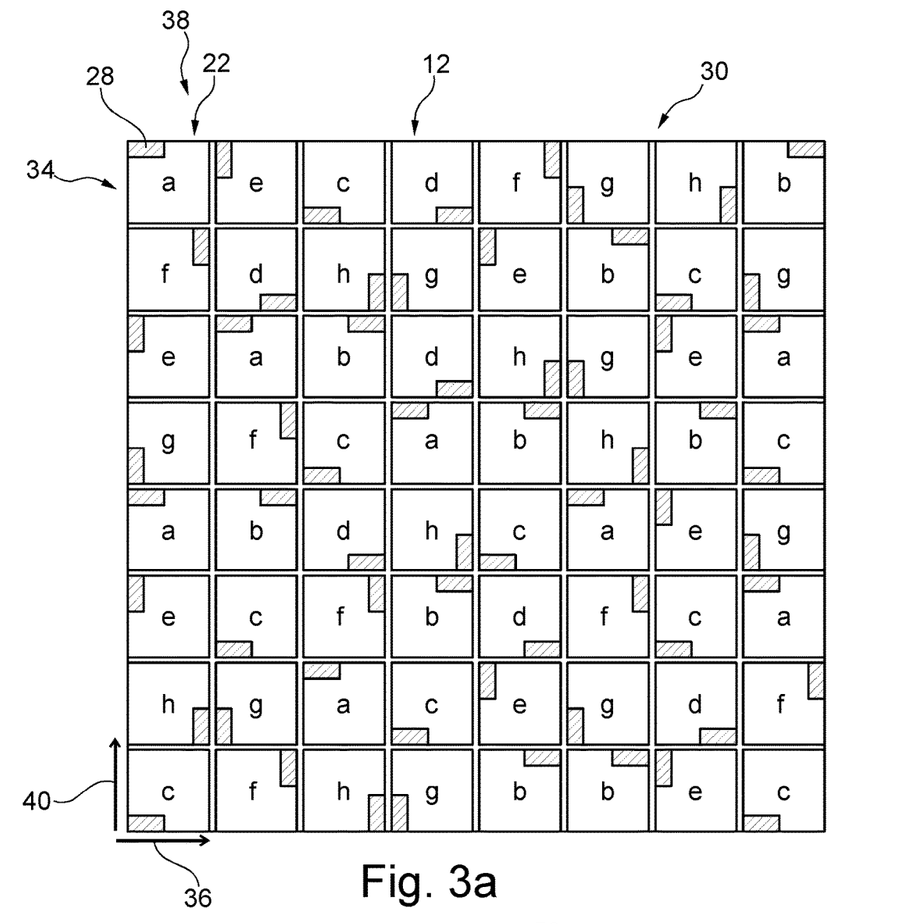
Figure 3B:
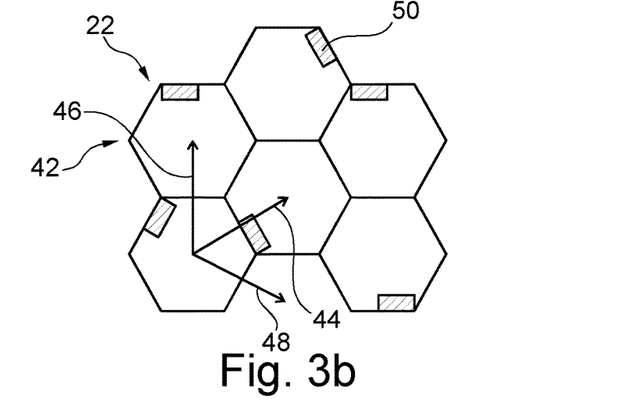

FIG. 3 shows two examples of a pixel array 12 with a number of pixels in a top view, one example in FIG. 3A and another example in FIG. 3B. The pixels each have the same layout scheme 22 but as different pixel layouts, which, for simplicity of the drawings, is indicated with a marked corner portion 28. Further, letters a, b, c, d, e, f, g, and h indicate different possible arrangements such that a pattern 30 is provided, in which at least a part of the pixels having the same pixel layout scheme 22 is provided such that the pixel layout of adjacent pixels is arranged differently.

For example, the pixel layout formed by the pixel layout scheme 22 of adjacent pixels can be mirrored and/or rotated, in relation to each other.

As mentioned above, the pixel itself may be provided with a square form, as also shown in FIG. 3A, or with a rectangle form or other form, such as a honeycomb form. The term "form" relates to the respective surface area of the pixel, i.e. the pixel comprised of the first part and the second part.

The sensitive areas may be provided with rectangular form, sometimes with one or more so-to-speak missing corner. The missing area, i.e. the surface not contributing to be sensitive to irradiation of X-rays, may be occupied by transistors and circuit paths, i.e. strip conductors.

The pixel itself may be provided in a rectangular form with a first pair of opposite sides having a smaller length than the second pair of opposite sides, or as a square form.

For example, the pixel has a rectangular form, such as a square or a rectangle, as indicted, for example, in FIG. 2B. The second part of the pixel's surface that is irrelevant to contributing to the sensitive area's signal, for example a photodiode's signal, is provided in a corner 32 of the pixel. The corner is also referred to as "blind pixel corner". The pixel may have a square form, as shown in FIG. 3A, or as a rectangular form.

Further, as also indicated in FIG. 3A, the pixels are provided in rows 34 in a first direction, indicated with an arrow 36, and in columns 38 in a second direction, as indicated with an arrow 40. A different arrangement of the layout is provided in the first and the second direction 36, 40, for the at least part of the pixels, for adjacent pixels.

The rows and columns 34, 38, are provided in two repetition directions, and the different arrangement is provided in both repetition directions.

FIG. 3A shows an example for an arrangement of pixels in rows and columns, and FIG. 3B shows the pixels provided in a honeycomb structure with three repetition directions.

As indicated in FIG. 3B, in another example the pixels 22 are provided in a honeycomb structure 42 with three repetition directions, indicated with a first arrow 44 for a first direction, a second arrow 46 for a second repetition direction, and a third arrow 48 indicating a third repetition direction. A different arrangement of the layout is provided in all three repetition directions for the at least part of the pixels, for adjacent pixels. The honeycomb pixels are once again indicated with a dotted corner 50.

Figure 4A:
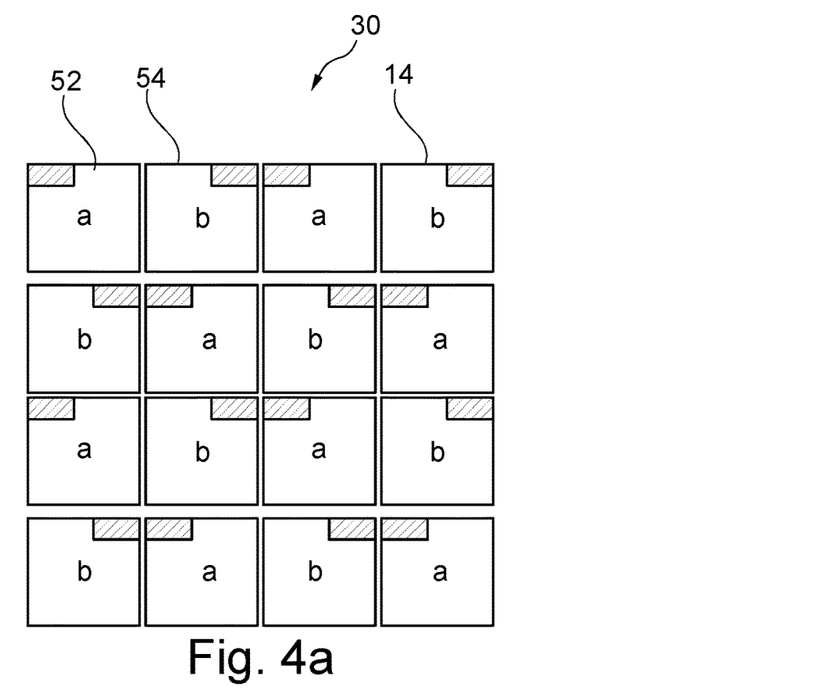
FIGS. 4A to 4C show different pixel arrangements for an X-ray detector.
Figure 4B:
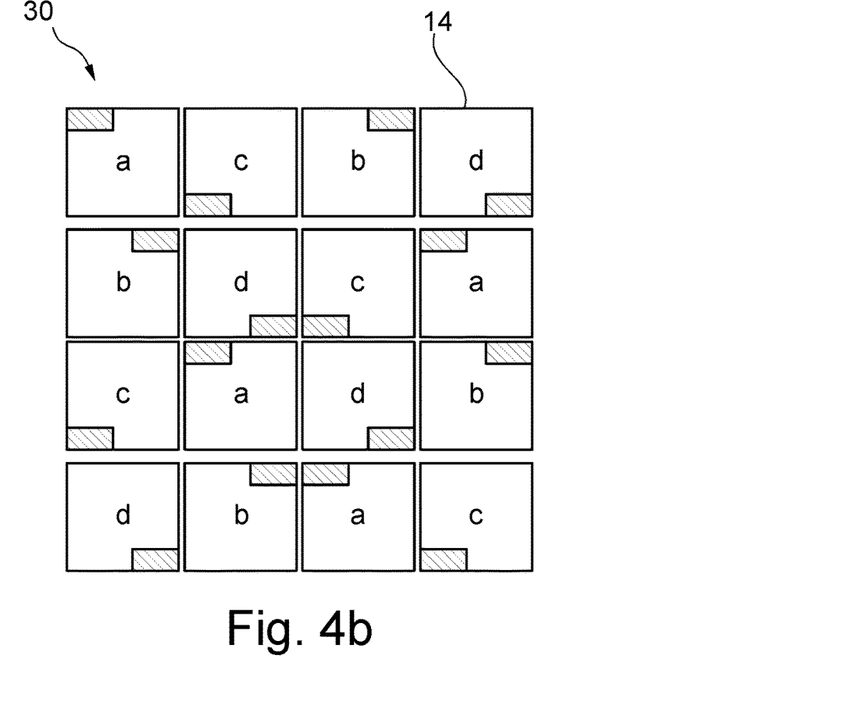
Figure 4C:
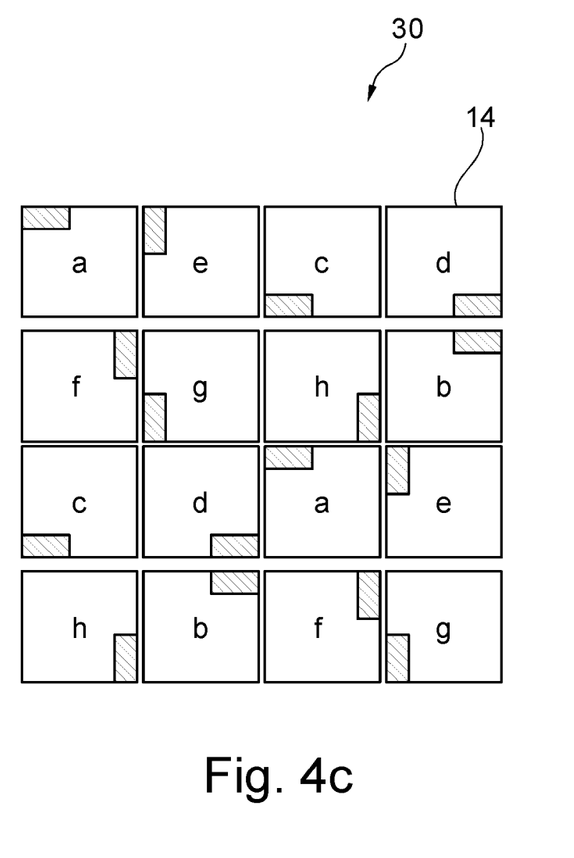

According to a further example, also applicable to FIGS. 3A and 3B, and also FIGS. 4A to 4C, for all pixels, adjacent pixel are provided in a different arrangement of the pixel layout, but with the same layout scheme.

As mentioned above, the term "different arrangement" relates to a different layout orientation, for adjacent pixels.

As shown in FIG. 4A, adjacent pixels can be provided mirrored with two pixel layouts, namely type "a" and type "b". For example, a first pixel 52 is having the layout type "a", and the adjacent pixel 54 is shown with a layout type "b".

FIG. 4A is showing a one axis mirroring resulting in the two pixel layouts, whereas FIG. 4B shows a two axes mirroring with resulting four pixel layouts, namely type "a", type "b", type "c", and type "d". The respective types are indicated in FIG. 4B.

FIG. 4C shows a further example, wherein a two axes mirroring together with a rotation has been applied, resulting in eight pixel layouts with types "a" to "h".

Further, it is also provided a pixel pattern in which the pixels are rotated resulting in different pixel layouts (not further shown).

For example, a pixel has four adjacent pixels, which are all different compared to the pixel to which they are adjacent to. In case of L-shaped active areas, eight different forms of arrangement can be provided. In case of a rectangular active area, two different forms of arrangement are provided. For example, a chessboard arrangement is provided.

For example, a group of three-by-three arrangements is repeated.

In another example, a random arrangement is provided to prevent cluster of similar pixel arrangements, as indicated, for example, in FIG. 3A.

The term "irrelevant" relates to not contributing to the photodiode's signal. A conversion element (scintillator) may be provided for each pixel for converting X-ray radiation into light visible by the photodiode, which light is converted into an electric signal by a (visible light) photodiode. This is also referred to as indirect detection.

The sensitive area may also be configured to convert X-ray radiation into an electric signal, which is also referred to as direct conversion. The sensitive area is provided as an electrode.

Figure 5:
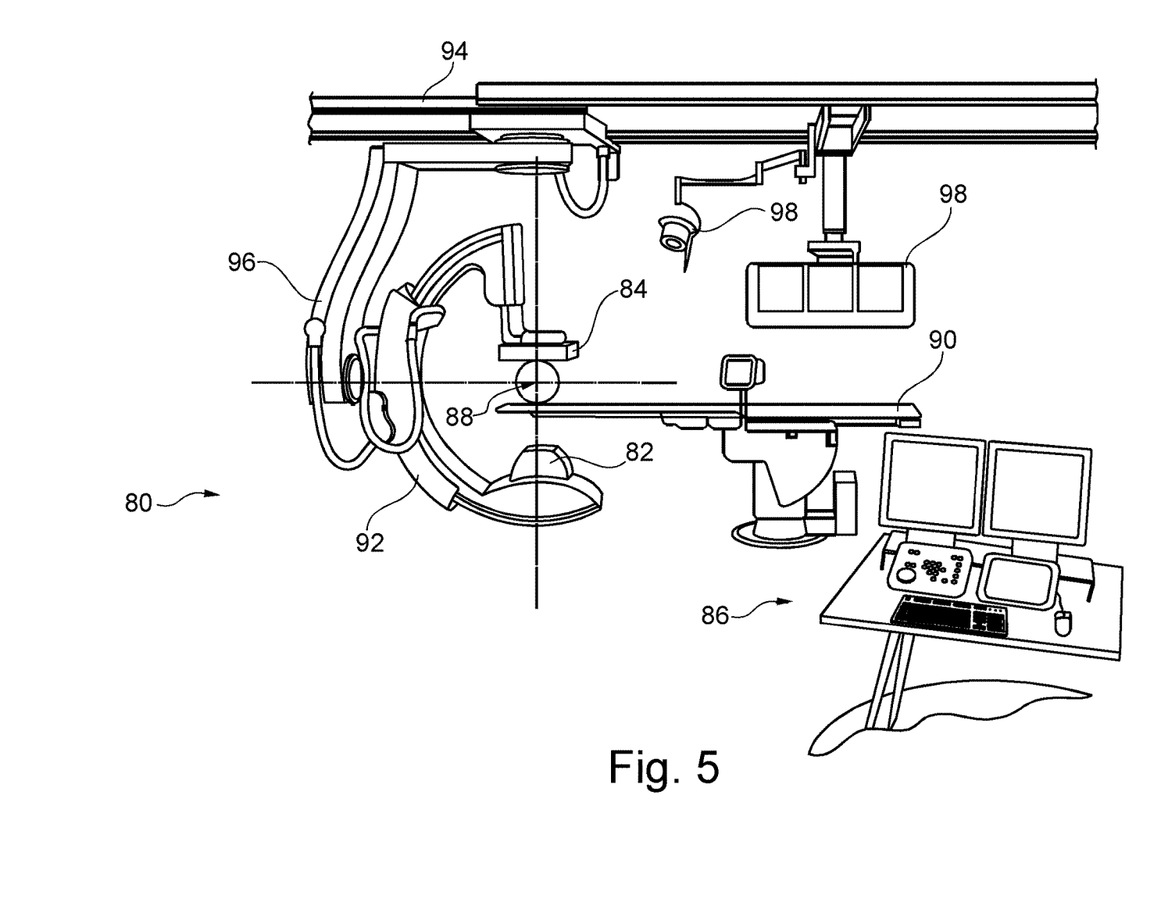
FIG. 5 shows a medical X-ray imaging system.

FIG. 5 shows a medical X-ray imaging system 80, comprising an X-ray source 82, an X-ray detector 84 and a processing unit 86. The X-ray detector 84 is provided as an X-ray detector according to one of the above mentioned examples.

Further, as an example, a patient 88 is provided on a patient table 90, which patient table may be adjustable in height, length and inclination.

The X-ray source 82 and the X-ray detector 84 are arranged on opposing ends of a C-arm structure 92, which is supported from a ceiling structure 94 by massive C-arm holding equipment 96.

Further, lighting and monitors 98 are also shown.

It must be noted that the X-ray imaging system 80 is shown as a C-arm type arrangement as an example only. Of course, other types of medical X-ray imaging systems are provided, such as a CT-system and the like.

Figure 6:
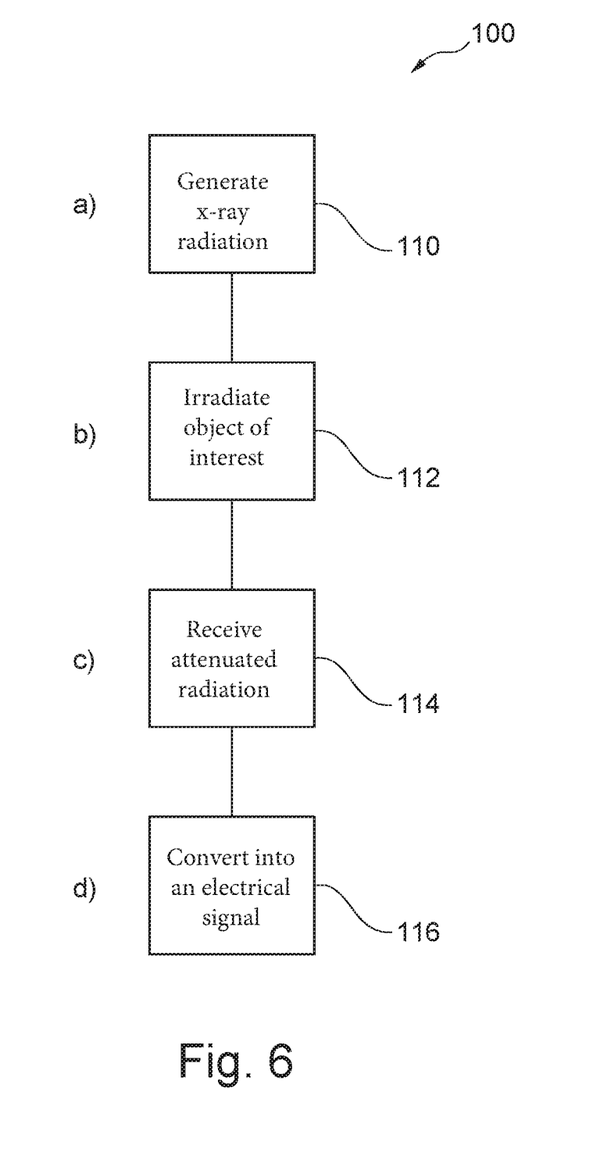
FIG. 6 shows basic steps of a method for X-ray imaging.

FIG. 6 shows a method 100 for X-ray imaging, comprising the following steps: In a first step 110, X-ray radiation is generated by an X-ray source. In a second step 112, an object of interest is radiated with at least a part of the generated X-ray radiation. In a third step 114, X-ray radiation has been received that was at least partly attenuated by the object. In a fourth step 116, the received X-ray radiation is converted into an electrical signal by an X-ray detector according to one of the above mentioned examples.

The first step 110 is also referred to as step a), the second step 112 as step b), the third step 114 as step c), and the fourth step 116 as step d).

According to an aspect, it is provided that an object, which is located at positions differently, relating to the position, has the same properties like contrast at another position. Thus, it is possible to shift the object on the detector without negative impact. In a wider interpretation, a rotation of an object is also expected to lead to similar signals. For example, if the detector is imaged with lines that are arranged to be smaller than the pixel width, such lines hit different portions of the detector, thus preventing and avoiding respective artifacts. To avoid scattered radiation, it is also possible to use an anti-scatter-grid on top of the detector. However, one compromise in this aspect is to use a grid with lamellas in a separation of the same order of magnitude as the pixel pitch of the detector; each grid lamella that is located exactly on top of a for example rectangular column of photo diodes will be depicted with a higher contrast than others. Due to this, a moiré pattern may become visible. With a pixel layout following the invention of the present application, the contrast of such patterns is lower of even zero.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray detector, comprising:
   a pixel array with a plurality of pixels, each of which comprises a sensitive area;
   a body structure; and
   an electric circuitry;
   wherein the sensitive areas are attached to the body structure;
   wherein the electric circuitry is provided to control and read out the sensitive areas and to connect the sensitive areas with a processing unit;
   wherein the sensitive areas are configured to provide an electric signal representing X-ray radiation hitting the pixel; and
   wherein all pixels are provided in a pixel layout with a pixel layout scheme where the sensitive area is a first part of the pixel's surface that is contributing to the pixel's signal and a second part of the pixel's surface is irrelevant to contributing to the pixel's signal; and
   wherein the sensitive areas are arranged on the body structure in a pattern in which at least a part of the pixels having the same pixel layout scheme is provided such that the pixel layout of adjacent pixels is arranged differently.

2. X-ray detector according to claim 1, wherein at least a part of the pixels is arranged such that the pixel layout of adjacent pixels is:
   i) mirrored, and/or
   ii) rotated,
   in relation to each other.

3. X-ray detector according to claim 1, wherein the first part of the pixel's surface is provided with a rectangular form.

4. X-ray detector according to claim 1, wherein the pixel has a rectangular form; and
   wherein the second part of the pixel's surface is provided in a corner of the pixel.

5. X-ray detector according to claim 1, wherein the pixels are provided in rows in a first direction and in columns in a second direction; and
   wherein a different arrangement of the layout is provided in the first and the second direction for the at least part of the pixels.

6. X-ray detector according to claim 1, wherein the pixels are provided in a honeycomb structure with three repetition directions; and
   wherein a different arrangement of the layout is provided in all three repetition directions for the at least part of the pixels.

7. A medical X-ray imaging system, comprising:
   an X-ray source;
   an X-ray detector; and
   a processing unit;
   wherein the X-ray detector is provided as an X-ray detector according to claim 1.

8. The medical X-ray system of claim 7, wherein the at least part of the pixels are divided among types of pixel layout such that, for any given one of said at least part of the pixels, the pixel layout type of an immediately neighboring pixel, from among said at least part of the pixels, is randomly different than that of said given pixel.

9. The medical X-ray system of claim 8, wherein said at least part of the pixels consists of at least 62 pixels.

10. A method for X-ray imaging, comprising the following steps:
    a) generating X-ray radiation by an X-ray source;
    b) radiating an object of interest with at least a part of the generated X-ray radiation;
    c) receiving X-ray radiation that was at least partly attenuated by the object; and
    d) converting the received X-ray radiation into an electrical signal by an X-ray detector according to claim 1.

11. The method of claim 10, wherein the at least part of the pixels are divided among types of pixel layout such that, for any given one of said at least part of the pixels, the pixel layout type of an immediately neighboring pixel, from among said at least part of the pixels, is randomly different than that of said given pixel.

12. The method of claim 1, wherein said at least part of the pixels consists of at least 62 pixels.

13. The X-ray detector of claim 1, wherein the at least part of the pixels are divided among types of pixel layout such that, for any given one of said at least part of the pixels, the pixel layout type of an immediately neighboring pixel, from among said at least part of the pixels, is randomly different than that of said given pixel.

14. The X-ray detector of claim 13, wherein said at least part of the pixels consists of at least 62 pixels.

15. An X-ray detector, comprising:
    a pixel array with a plurality of pixels, each of which comprises a sensitive area;
    a body structure; and
    an electric circuitry;
    wherein the sensitive areas are attached to the body structure;
    wherein the electric circuitry is provided to control and read out the sensitive areas and to connect the sensitive areas with a processing unit;
    wherein the sensitive areas are configured to provide an electric signal representing X-ray radiation hitting the pixel; and
    wherein all pixels are provided in a pixel layout with a pixel layout scheme where the sensitive area is a first part of the pixel's surface that is contributing to the pixel's signal and a second part of the pixel's surface is irrelevant to contributing to the pixel's signal; and
    wherein the sensitive areas are arranged on the body structure in a pattern in which, for all pixels, adjacent pixels are provided in a different arrangement of the pixel layout, but with the same pixel layout scheme.

16. X-ray detector according to claim 15, wherein all pixels are arranged such that the pixel layout scheme of adjacent pixels is i) mirrored, and/or ii) rotated, in relation to each other.

* * * * *